(12) United States Patent
Guinn et al.

(10) Patent No.: US 6,194,429 B1
(45) Date of Patent: Feb. 27, 2001

(54) ALATROFLOXACIN PARENTERAL COMPOSITIONS

(75) Inventors: Robert Mark Guinn, Mystic; John Francis Lambert, North Stonington; Subramanian Sam Guhan, Niantic; Stanley Walter Walinsky, Mystic, all of CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/403,886

(22) PCT Filed: Jul. 23, 1998

(86) PCT No.: PCT/IB98/01122

§ 371 Date: Oct. 27, 1999

§ 102(e) Date: Oct. 27, 1999

(87) PCT Pub. No.: WO99/06430

PCT Pub. Date: Feb. 11, 1999

Related U.S. Application Data (60) Provisional application No. 60/054,246, filed on Aug. 1, 1997.

(51) Int. Cl.[7] ............ A61K 31/44; C07D 471/02
(52) U.S. Cl. ............................... 514/300; 546/123
(58) Field of Search .............................. 514/300; 546/123

(56) References Cited

U.S. PATENT DOCUMENTS

| 5,164,402 | 11/1992 | Brighty . |
| 5,229,396 | 7/1993 | Brighty . |
| 5,256,791 | 10/1993 | Braish . |
| 5,475,116 | 12/1995 | Brighty et al. . |
| 5,728,711 | 3/1998 | Girard et al. . |
| 5,939,550 * | 8/1999 | Braish ................................ 546/123 |

FOREIGN PATENT DOCUMENTS

| 0287926 | 4/1988 | (EP) . |
| 0818445 | 7/1997 | (EP) . |
| 9519361 | 7/1995 | (WO) . |
| 9639406 | 12/1996 | (WO) . |
| 9700268 | 1/1997 | (WO) . |
| 9707800 | 3/1997 | (WO) . |
| 9708191 | 3/1997 | (WO) . |
| 9719921 | 6/1997 | (WO) . |

* cited by examiner

*Primary Examiner*—D. Margaret Seaman
(74) *Attorney, Agent, or Firm*—Peter C. Richardson; Paul H. Ginsburg; Seth H. Jacobs (57) ABSTRACT

The present invention relates to alatrofloxacin mesylate substantially free of less polar impurities, to parenteral compositions of alatrofloxacin mesylate and to processes for purifying alatrofloxacin mesylate.

25 Claims, 4 Drawing Sheets

ALATROFLOXACIN PARENTERAL COMPOSITIONS

This application is a 371 of PCT/IB 98/01122, filed Jul 23, 1998 and claims the benefit of priority of provisional application Ser. No. 60/054,246, filed Aug. 1, 1997.

BACKGROUND OF THE INVENTION

The present invention relates to the naphthyridone antibiotic alatrofloxacin mesylate essentially free of less polar impurities, to parenteral compositions of said alatrofloxacin mesylate and to processes for purifying alatrofloxacin mesylate.

Alatrofloxacin mesylate is the mesylate prodrug salt of related naphthyridone antibiotic trovafloxacin. Alatrofloxacin mesylate, prepared by methods currently available is produced in very high purity. However, alatrofloxain mesylate prepared by these current methods contains minute less polar impurities that tend to precipitate from parenteral compositions after standing for indefinite periods. These less polar impurities can not be adequately removed by commercially feasible methods such as recrystallization, standard chromatographic means using flash silica gel, solventisolvent extraction methods, or by treatment with diatomaceous earth. The present inventors have discovered that the impurities can be successfully removed by treating the crude reaction products, i.e. product prepared by any of the currently known literature methods, with a polystyrene resin.

It has been previously known that the quinolone antibiotic ciprofloxacin also possesses impurities rendering the product unsuitable for parenteral formulation. European Patent Publication 287,926, published Oct. 26, 1988, describes the purification of ciprofloxacin by treatment with diatomaceous earth so as to yield a product that is suitable for parenteral formulation. As stated above, treatment of alatrofloxacin mesyiate with diatomaceous earth does not adequately remove the less polar impurities.

The antibacterial activity and synthesis of the aforementioned alatrofloxacin are described in U.S. Pat. Nos. 5,164,402 and 5,229,396 issued Nov. 17, 1992 and Jul. 20, 1993, respectively, the disclosures of which are hereby incorporated herein by reference in their entirety. The foregoing patents are assigned in common with the present application.

International Patent Publication WO 97/00268, published Jan. 3, 1997, claims an alternative process for preparing alatrofloxacin. The foregoing publication is hereby incorporated by reference in its entirely.

International Patent Publication WO 97/08191, published Mar. 6, 1997, describes a third process for the preparation, and polymorphs thereof, of alatrofloxacin, the disclosure of which is hereby incorporated herein by reference in its entirety. The foregoing patent publication is assigned in common with the present application.

International Patent Publication WO 95/19361, published Jul. 20 1995; U.S. patent application No. 60/021,419, filed Jul. 9, 1996; and International Patent Application No. PCT/EP96/04782, filed Oct. 31, 1996, claim novel intermediates for preparing alatrofloxacin and trovafloxacin, the disclosures of which are hereby incorporated herein by reference in their entirety. The foregoing patent publications and applications are assigned in common with the present application.

U.S. Pat. No. 5,475,116, issued Dec. 12, 1995, and U.S. Pat. No. 5,256,791, issued Oct. 26, 1993, claim various azabicyclohexane intermediates useful in the synthesis of alatrofloxacin and trovafloxacin, the disclosures of which are hereby incorporated herein by reference in their entirety. The foregoing patents are assigned in common with the present application.

U.S. patent application Ser. No. 08/764,655, filed Dec. 2, 1996, refers to methods of treating *Helicobacter pylori* infections with alatrofloxacin and trovafloxacin, the disclosure of which is hereby incorporated herein by reference in its entirety. The foregoing patent application is assigned in common with the present application.

International Patent Publication WO 96/39406, published Dec. 12, 1996 claims a novel crystal form of anhydrous 7-([1α,5α,6α]-6-amino3-azabicyclo[3.1.0]hex-3-yl)6-fluoro-1-(2,4-difluorophenyl)-1,4-dihydro4-oxo-1,8-naphthyridine-3-carboxylic acid, methanesulfonic acid salt, a method of using said compound in the treatment of a bacterial infection in mammals, especially humans, and to pharmaceutical compositions, the disclosure of which is hereby incorporated herein by reference in its entirety. The foregoing patent publication is assigned in common with the present application.

International Patent Application PCT/IB 96/00756, filed Jul. 29, 1996, claims zwitterionic forms of trovafloxacin which are useful for the administration of the drug as a suspension, the disclosure of which is hereby incorporated herein by reference in its entirety. The foregoing patent application is assigned in common with the present application.

SUMMARY OF THE INVENTION

The present invention relates to a process of purifying a compound of the formula comprising treating an impure reaction product containing an amount of said compound of formula I and less polar impurities, with a hydrophobic resin. Said less polar impurities are defined by their high pressure liquid chromatography (HPLC) retention times from injection of a sample in a Hewlett-Packard Model 1100 Series High Pressure Liquid Chromatographer® eluting with a mobile phase solution of 40% acetonitrile, 0.05M potassium dihydrogen phosphate ($KH_2PO_4$) and 0.3% perchloric acid (V/V) at a flow rate of about 2 ml per minute on a Puresil® 5 micron $C^{18}$ silica HPLC column (4.6×150 mm) with a 20 μl injection volume and with a Hewlett-Packard 1100 Series Diode Array Detector® with the detector set to record at a wavelength of 270 nm. The HPLC column is used at ambient temperature (20–25° C.). Said less polar impurities, defined by the aforesaid HPLC conditions, have a retention time of about 2.1 minutes to about 30 minutes. One particular undesirable less polar impurity has a retention time of 9–12 minutes, under the aforesaid HPLC conditions. The aforesaid impurity with the retention time of 9–12 minutes has the formula

II (hereinafter also referred to as the "oligomer impurity"). Preferably, the less polar impurities, after treatment, comprise less than 500 ppm, more preferably less than 60 ppm, relative to the weight of the crude product. Most preferably, said impurities comprise less than 20 ppm. Preferably, the hydrophobic resin is a crosslinked polystyrene resin such as Diaion HP-20® or Amberchrom CG-161®.

The present invention also relates to a compound of the formula

I substantially free of less polar impurities, more preferably substantially free of the compound of formula II.

The present invention also relates to a parenteral composition, comprising an antibacterially effective amount of a compound of the formula I, or a pharmaceutically acceptable salt thereof, substantially free of less polar impurities, preferably substantially free of a compound of formula II, and a pharmaceutically acceptable carrier. Preferably, the pharmaceutically acceptable carrier is water.

The present invention also relates to a parenteral composition, as described above, wherein the compound of formula I is a lyophylate.

The present invention also relates to a pharmaceutical composition, as described above, wherein the compound of formula I comprises about 10 mg to about 700 mg, preferably about 275 mg to about 500 mg of compound in a unit dosage container, most preferably about 300 mg.

The present invention also relates to a compound of the formula

II

The present invention also relates to a pharmaceutical composition, comprising an antibacterially effective amount of a compound of formula II, or a pharmaceutically acceptable salt thereof.

The present invention also relates to a method of treating a bacterial infection, comprising administering to a subject affected by a bacterial infection an antibacterially effective amount of a compound according to formula II.

The present invention also relates to a compound of the formula

III

The present invention also relates to a pharmaceutical composition, comprising an antibacterially effective amount of a compound of formula III, or a pharmaceutically acceptable salt thereof.

The present invention also relates to a method of treating a bacterial infection, comprising administering to a subject affected by a bacterial infection an antibacterially effective amount of a compound of formula Ill.

DETAILED DESCRIPTION OF THE INVENTION

Alatrofloxacin may be prepared by three methods which have been described in issued patents or patent publications. Specifically, alatrofloxacin can be prepared by coupling a BOC-(L-Ala-L-Ala)-azabicyclohexane with an activated quinolone as described in U.S. Pat. No. 5,164,402, issued Nov. 17, 1992, and U.S. Pat. No. 5,229,396, issued Jul. 20, 1993. A second method of preparing alatrofloxacin involves reaction of BOC-L-Ala-L-Ala with a protected azabicyclohexane-naphthyridine nucleus as described in International Patent Publication WO 97/00268, published Jan. 3, 1997. Finally, the third method for producing alatrofloxacin involves coupling of trovafloxacin mesylate with BOC-L-Ala-L-Ala as described in International Patent Publication WO 97/08191, published Mar. 6, 1997. The disclosures of each of the aforementioned patents or patent publications are hereby incorporated herein by reference in their entirety. The foregoing patents and patent publications are assigned in common with the present application.

Figure 1:
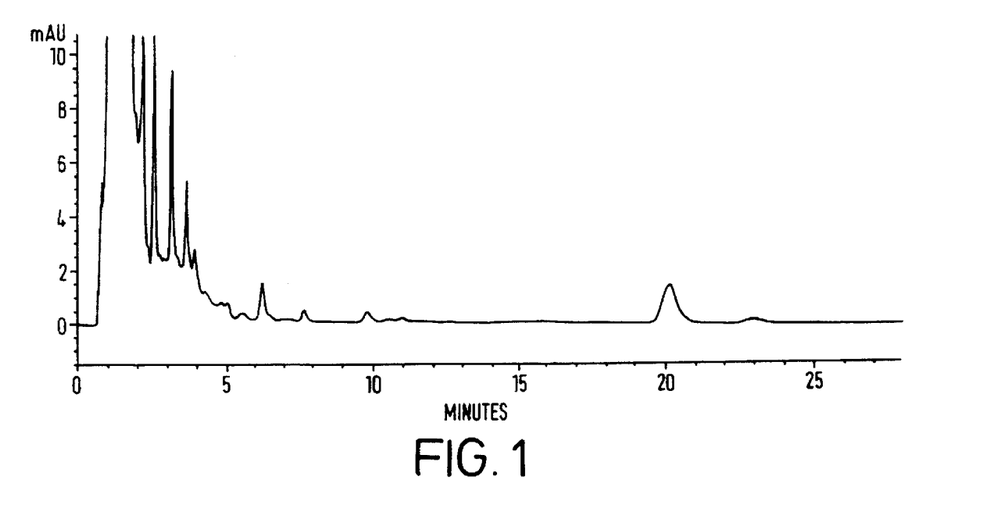
Figure 2:
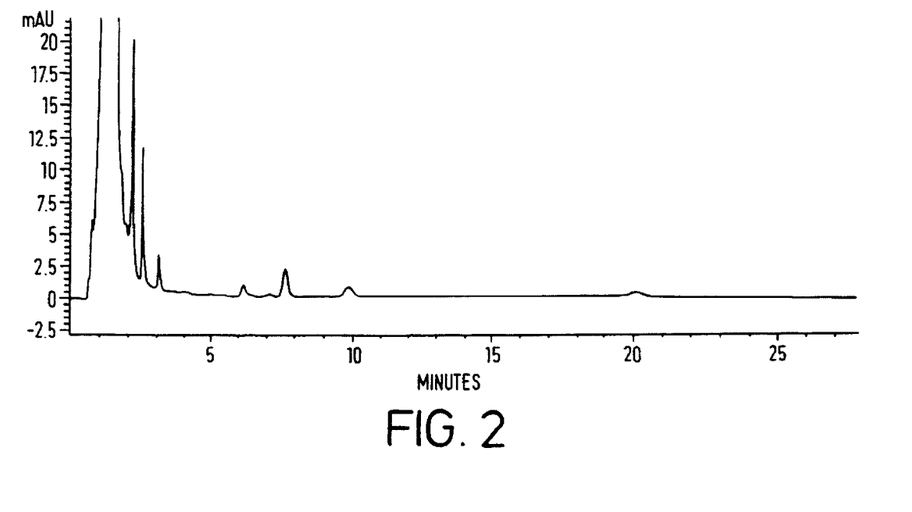
Figure 3:
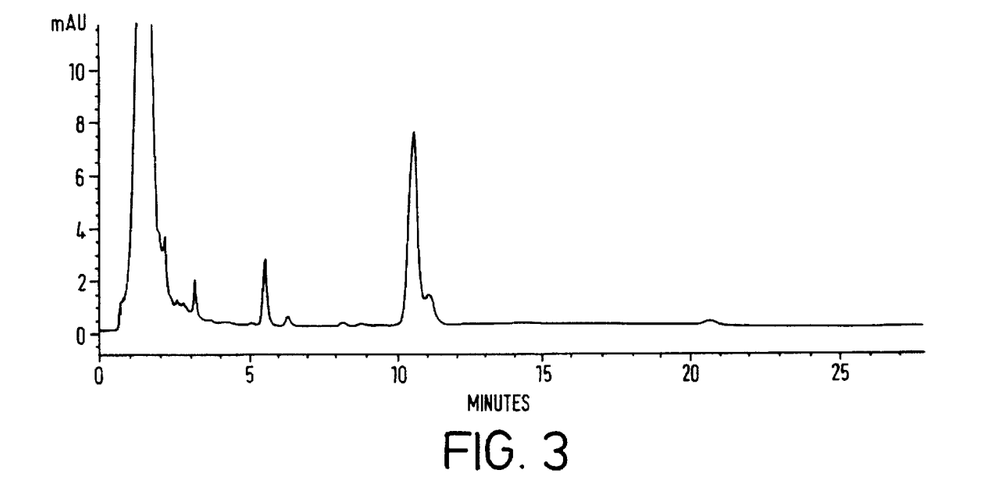

Crude alatrofloxacin, prepared by any of the aforementioned methods, contains small amounts of less polar impurities. The specific type and amount of impurity depends on the process and conditions used. Crude alatrofloxacin drug products prepared according to each of the above three procedures have characteristic HPLC chromatograms, when recorded according to the aforesaid conditions, that are depicted in FIGS. 1–3, respectively. Specifically, FIG. 1 describes a chromatogram of alatrofloxacin mesylate prepared according to the methods described in Brighty, et al., U.S. Pat. No. 5,164,402, issued Nov. 17, 1992, and U.S. Pat. No. 5,229,396, issued Jul. 20, 1993. The approximate concentration of the impurities of this original method, when normalized to a known concentration of oligomer, are presented in Table 1, below. FIG. 2 describes a HPLC chromatogram of the alatrofloxacin mesylate prepared according to the methods described in International Patent Publication WO 97/00268, published Jan. 3, 1997. The approximate concentration of the impurities produced by this second method, when normalized to a known concentration of oligomer, are presented in Table 2, below. FIG. 3 describes a HPLC chromatogram of the alatrofloxacin mesylate prepared according to the methods described in International Patent Publication WO 97108191, published Mar. 6, 1997. The approximate concentration of the impurities produced according to this third method, when normalized to a known concentraion of oligomer, are presented in Table 3, below. As stated above, said less polar impurities are defined by their retention time from injection of a sample in a Hewlett-Packard Model 1100 Series High Pressure Liquid Chromatograph® eluting with a mobile phase solution of 40% acetonitrile, 0.05M potassium dihydrogen phosphate ($KH_2PO_4$) and 0.3% perchloric acid (V/V) at a flow rate of about 2 ml per minute on a Puresil® 5 micron $C^{18}$ silica column (4.6×150 mm) with a 20 µl injection volume and with a Hewlett-Packard 1100 Series Diode Array Detector® with the detector set to record at a wavelength of 270 nm. Said less polar impurities defined by the aforesaid conditions have a retention time of about 2.2 minutes to about 30 minutes. One particular undesirable impurity has a retention time of 9–12 minutes (approximately 10.5 minutes), under the aforesaid conditions. The aforesaid impurity with the retention time of 9–12 minutes has the formula This impurity comprises about 700 ppm of the reaction product produced according to the third method described above. The absolute amount of the impurity depends on the process and conditions used. After purification, this impurity comprises less than about 100 ppm of the reaction product, preferably less than 50 ppm, most preferably less than about 20 ppm.

Other impurities have retention times of about 23.0, 20.1, 13.6, 11.7, 11.0, 10.9, 9.8, 8.4, 7.6, 7.1, 6.2, 5.5, 5.0, 4.8, 3.9, 3.6, 3.1, 2.8, 2.5 and 2.1 minutes, according to the conditions described above. The compounds corresponding to these retention periods have not as of yet been characterized due to their low ppm concentration.

These impurities can be removed by resin chromatography, eluting with a polar solvent. Specifically, the reaction product is dissolved in a small amount of water. The dissolved crude reaction product is then added to a column packed with a polystyrene resin, such as hydrated Amberchrom CG-161® polystyrene resin (Tosohaas Chemicals 156 Keystone Drive, Montgomeryville, Pa. 18936), Amberlite® XAD4 or XAD-16 (Rohm and Haas) or Diaion HP-20® (Mitsubishi Chemical Co.), preferably hydrated Amberchrom CG-161® polystyrene resin. Polystyrene resins are hydrophobic macroporous styrenic based polymeric bead type resins which provide non-polar aromatic surfaces for adsorption. Those of ordinary skill in the art will understand that non-ionic polymeric resins are available in various bead sizes, pore sizes, and surface areas that influence separation conditions. One of ordinary skill in the art will also understand that the resin parameters may be varied to optimize the results for a specific application. The weight ratio of crude reaction product (kilogram) to weight of dry resin (kilogram) is from about 8 to about 15 kilograms crude reaction product to about one kilogram dry resin. Preferably, the ratio of the weight of crude reaction product to the weight of resin is approximately 10–12 kg of crude reaction product per kilogram of dry resin. The ratio of the volume of eluant (liters) to the weight of crude drug substance (kilogram) varies from about 1 to about 70 liters of solvent per kilogram crude drug substance, preferably 10 to 40 liters of water per kilogram of drug substance at ambient temperature. Most preferably, about 25 liters of water per kilogram of drug substance at ambient temperature elutes pure product. The flow rate of the eluant through the column is in the range of 1–10 bed volumes per hour (i.e. the amount of eluant required to fill and empty the resin bed in one hour). Preferably, the flow rate of eluant solution is 3–5 bed volumes per hour.

Figure 4:
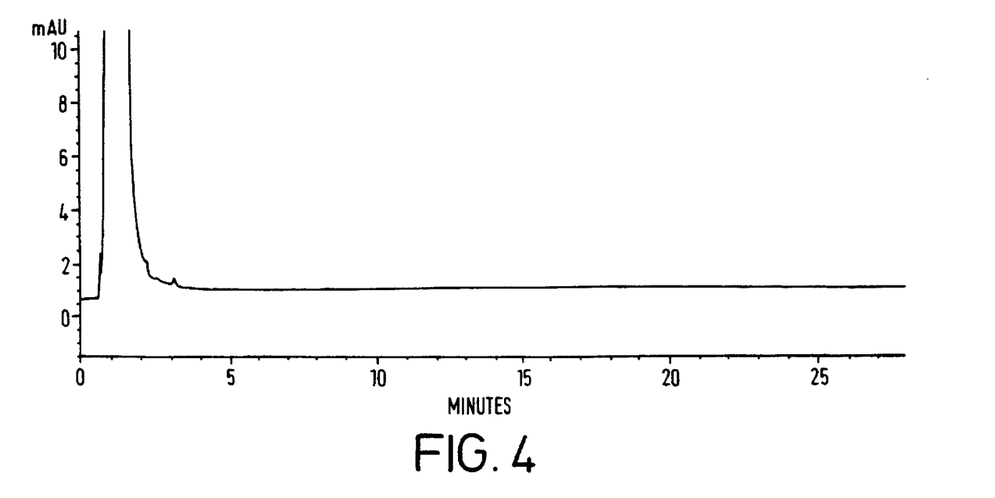
Figure 5:
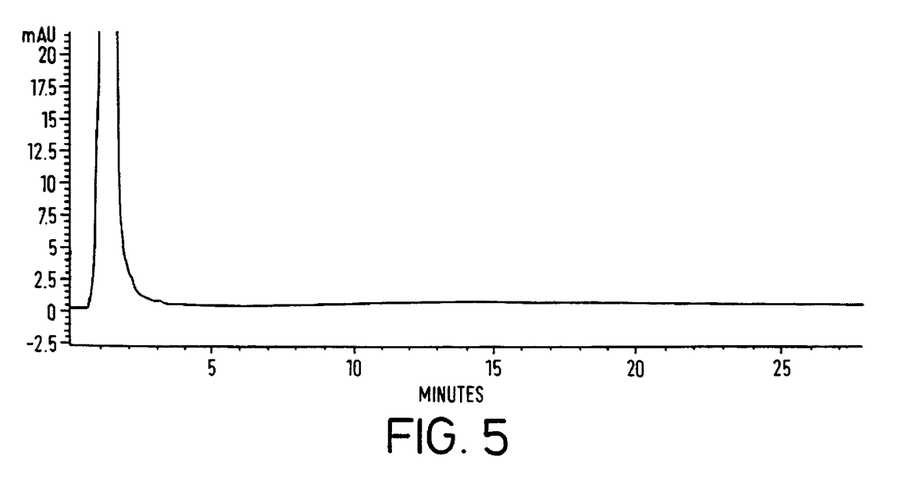
Figure 6:
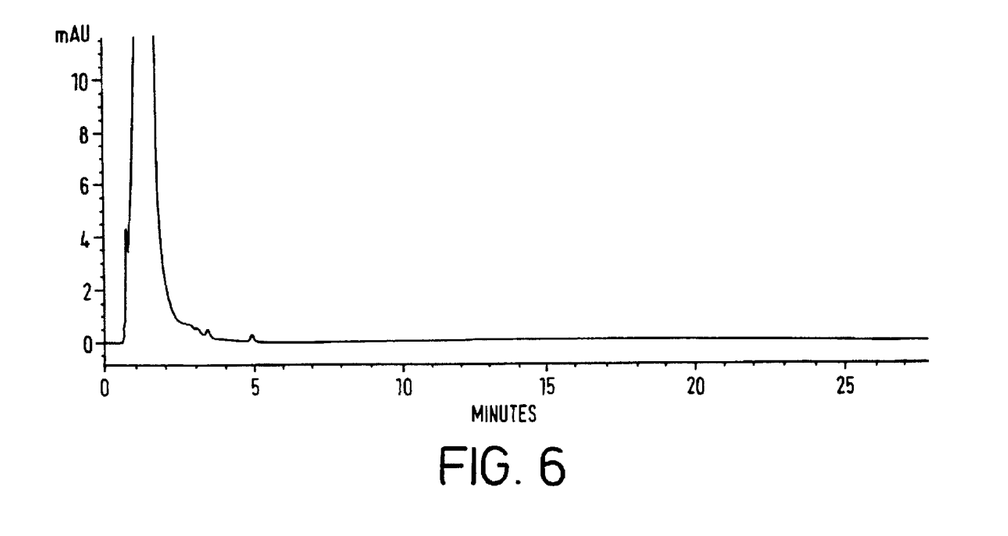

The product prepared according to the methods described above is essentially free of less polar impurities and is suitable for use as a parenteral composition. Purified alatrofloxacin mesylate, wherein the starting materials are the crude alatrofloxacin drug products prepared according to the above three procedures, have HPLC chromatograms, when recorded according to the aforesaid conditions, that are depicted in FIGS. 4–6, respectively. Specifically, FIG. 4 describes a chromatogram of purified alatrofloxacin mesylate, after resin treatment, prepared by treating the crude alatrofloxacin mesylate prepared according to the methods described in Brighty, et al., U.S. Pat. No. 5,164,402 issued Nov. 17, 1992, and U.S. Pat. No. 5,229,396 issued Jul. 20, 1993. The approximate concentration of the impurities after purification, when normalized to a known amount of oligomer are presented in Table 1, below. FIG. 5 describes a HPLC chromatogram of purified alatrofloxacin mesylate prepared by treating the crude alatrofloxacin mesylate prepared according to the methods described in International Patent Publication WO 97/00268, published Jan. 3, 1997. The approximate concentration of the impurities after purification, when normalized to a known amount of oligomer are presented in Table 2, below. FIG. 6 describes a HPLC chromatogram of purified alatrofloxacin mesylate prepared by treating the crude alatrofloxacin mesylate prepared according to the methods described in International Patent Publication WO 97/08191, published Mar. 6, 1997. The approximate concentration of the impurities after purification, when normalized to a known amount of oligomer are presented in Table 3, below.

TABLE 1

| Retention Time (minutes) | Concentration Before Resin Treatment (ppm) | Concentration After Resin Treatment (ppm) |
| --- | --- | --- |
| 2.1 | 214 | |
| 2.5 | 250 | 1 |
| 3.1 | 197 | 5 |
| 3.6 | 94 | |
| 3.9 | 34 | |
| 4.8 | 16 | |
| 5.0 | 17 | |
| 5.5 | 17 | |
| 6.2 | 83 | |
| 7.6 | 27 | |
| 9.8 | 30 | |
| 10.5 | 8 | |
| 10.9 | 10 | |

TABLE 1-continued

| Retention Time (minutes) | Concentration Before Resin Treatment (ppm) | Concentration After Resin Treatment (ppm) |
| --- | --- | --- |
| 20.1 | 211 | |
| 23.0 | 29 | |

TABLE 2

| Retention Time (minutes) | Concentration Before Resin Treatment (ppm) | Concentration After Resin Treatment (ppm) |
| --- | --- | --- |
| 2.1 | 382 | |
| 2.5 | 234 | |
| 3.1 | 77 | 2 |
| 5.5 | 7 | |
| 6.2 | 55 | |
| 7.1 | 10 | |
| 7.6 | 118 | |
| 8.4 | 4 | |
| 9.8 | 76 | |
| 11.7 | 5 | |
| 13.6 | 5 | |
| 20.1 | 49 | |

TABLE 3

| Retention Time (minutes) | Concentration Before Resin Treatment (ppm) | Concentration After Resin Treatment (ppm) |
| --- | --- | --- |
| 2.1 | 28 | |
| 2.5 | 8 | |
| 2.8 | 5 | |
| 3.1 | 38 | 5 |
| 5.0 | 5 | |
| 5.5 | 124 | 13 |
| 6.2 | 22 | |
| 8.4 | 8 | |
| 10.5 | 700 | |
| 11.0 | 97 | |
| 20.1 | 22 | |

Figure 7:
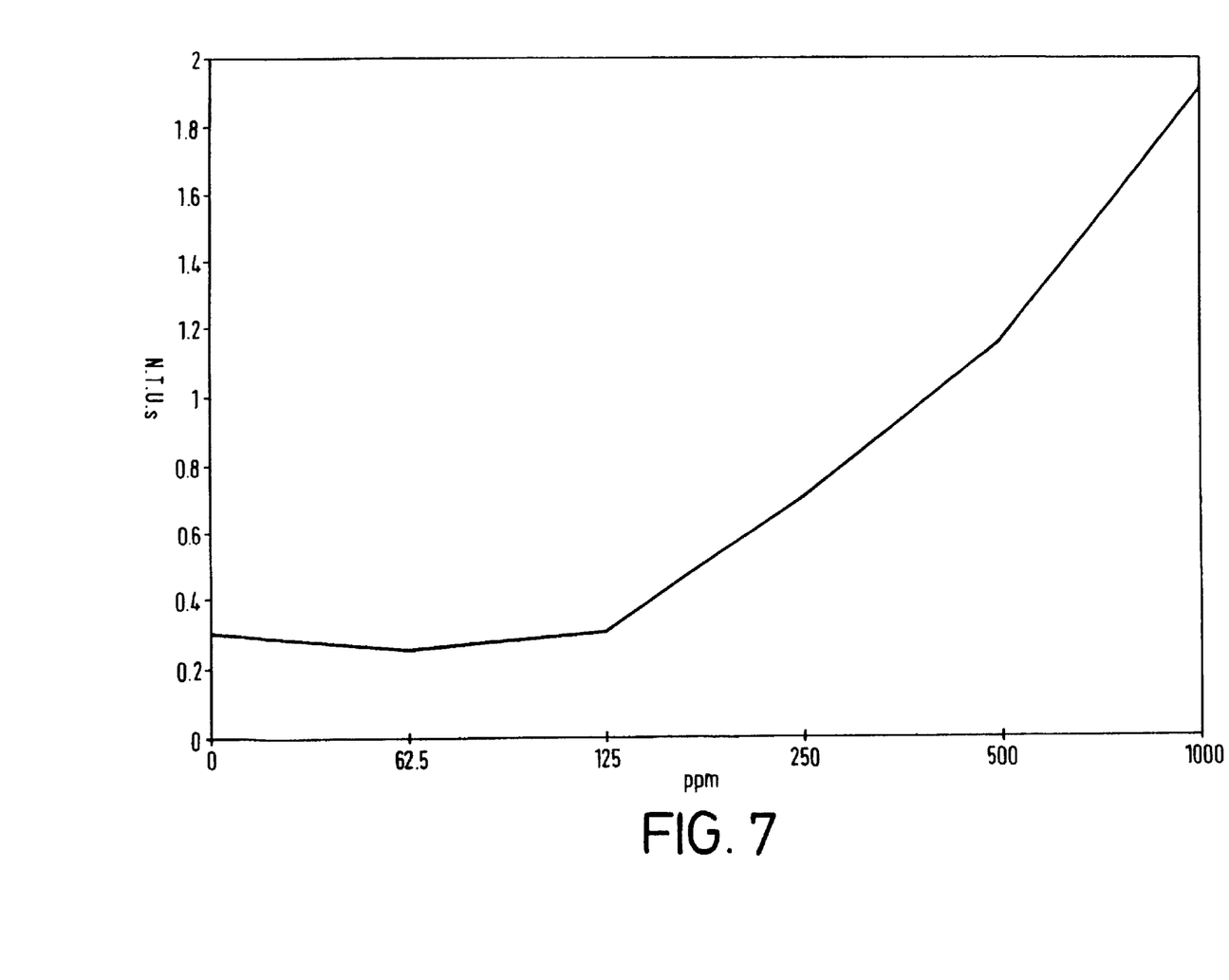

Parenteral compositions are more affected by trace contaminants than other pharmaceutical compositions. This is so because parenteral compositions, whether diluted or reconstituted, are liquid dosage forms whose quality standards are evident to visual inspection. Visual inspection of parenteral compositions can detect less polar impurities as low as 10 ppm. Presence of visible impurities affect the public's confidence in the safety, stability and use of a product. It is therefore important to remove as many less polar impurities as possible from parenteral compositions since less polar impurities are generally less aqueous soluble and more likely to precipitate from the formulation. Furthermore, most industrial nations require that parenteral compositions under consideration for drug approval meet a minimum standard for purity and absence of particulate contamination. The minimum standard in the United States is that the parenteral composition "be essentially free from particles that can be observed on visual inspection", *United States Pharmacopeia,* R-246 (1994). The United States Pharmacopeia (USP) does not provide specifications for the minimum amount of particulate matter, i.e. impurities, that would satisfy this standard. The USP does provide several tests for enumerating subvisible extraneous particles which are helpful in qualifying the amount of particulate matter. However, none of these tests are sufficient to satisfy the standard that the composition should be "essentially free from particles that can be observed on visual inspection." Although no one test is accepted as certifying the purity of a composition, turbidity analysis is one commonly accepted measure for quantifying the presence of particulate matter, see W. J. Passl et al., *Analyst,* 105, 512–515 (1980). According to standard turbidity measures, a value of 0–0.45 Nephelometric Turbidity Units (NTU) is accepted as a solution free of particulate matter. The product of the present invention when analyzed by a common turbidometric apparatus, Hellige Turbidimeter, (Hellige, Inc. 877 Stewart Avenue, Garden City, N.Y. 11530) routinely yielded turbidity measures as low as 0.3 NTU. The crude starting material, produced according to the process described in International Patent Publication WO 97/08191, yielded turbidity measures as high as about 1 NTU. FIG. 7 shows the relationship of turbidity as a function of impurity concentration (ppm of oligomer relative to crude material). The process of the present invention includes all compositions having a turbidity measure less than 0.5 NTU.

The product so purified can be formulated for parenteral administration (e.g., intravenous, intramuscular or subcutaneous) to mammals, including humans, for the treatment of bacterial infections by methods well known to those of ordinary skill in the art or by the methods described below. In general, the compound of formula I will be administered at dosages between about 0.5 to about 16 mg/kg/day, preferably about 4–7 mg/kg/day most preferably about 4.5 mg/kg/day. However, some variation in dosage will necessarily occur depending on the condition of the subject being treated. The person responsible for administration will, in any event, determine the appropriate dose for the individual subject.

The alatrofloxacin mesylate of the present invention can be administered in a wide variety of different dosage forms, in general, the therapeutically effective compounds of this invention are present in such dosage forms at concentration levels ranging from about 0.5% to about 70% (100% for lyophylate) by weight. For parenteral administration (intramuscular, intraperitoneal, subcutaneous and intravenous use) a sterile pyrogen free injectable solution of the active ingredient is usually prepared. Solutions of the compound of formula II, substantially free of less polar impurities, preferably the compound of formula II, can be prepared in a solvent such as sesame oil, peanut oil, water or aqueous propylene glycol. Preferably the solution is unbuffered water. The aqueous solutions can also be suitably adjusted and buffered, if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those of ordinary skill in the art. In the case of animals, compounds can be administered intramuscularly or subcutaneously at dosage levels of about 0.1 to 20 mg/kg/day, preferably about 0.2 to about 10 mg/kg/day given in a single dose or up to 3 divided doses.

The compound of formula II when hydrolyzed in vitro to remove the L-Ala-L-Ala dipeptide group, also possesses antibacterial activity. Such hydrolyzed compound has the formula

III

The antibacterial activity of the compound of formula III can be determined according to methods well known to those of ordinary skill in the art, such as those described in E. Steers et al., *Antibiotics and Chemotherapy*, 9, 307 (1959). The compound of formula III when assayed according to the method described above yielded an Minimum Inhibitory Concentration (MIC) of 6.25 μg/ml against *Streptococcus pyogenes* and 12.5–25 μg/mL against a number of *Staphylococcus aureus* strains.

The compound of formula III can be formulated in a conventional manner using one or more pharmaceutically acceptable carriers. Thus, the compound of formula III may be formulated for oral, buccal or rectal administration.

For oral administration, the pharmaceutical compositions of the compound of formula III may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g, lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition of the compound of formula III may take the form of tablets or lozenges formulated in conventional manner.

The compound of formula III may also be formulated in rectal compositions such as suppositories or retention enemas, e.g., containing conventional suppository bases such as cocoa butter or other glycerides.

A proposed dose of the compound of formula III for oral, rectal or buccal administration to the average adult human for the treatment of a bacterial infection is between about 0.1 to about 500 mg/kg/day, preferably from about 0.5 to about 50 mg/kg/day of the active ingredient per unit dose which could be administered, for example, 1 to 4 times per day.

The following Examples illustrate the preparation of the compound and compositions of the present invention. Melting points are uncorrected. NMR data are reported in parts per million (δ) and are referenced to the deuterium lock signal from the sample solvent (deuteriodimethylsulfoxide unless otherwise specified). Commercial reagents were utilized without further purification. DMF refers to N,N-dimethylformamide. Chromatography refers to high pressure liquid chromatography on a Hewlett-Packard Model 1100 Series High Pressure Liquid Chromatograph® eluting with a mobile phase solution of 40% acetonitrile, 0.05M potassium dihydrogen phosphate ($KH_2PO_4$) and 0.3% perchloric acid (V/V) at a flow rate of about 2 ml per minute on a Puresil® 5 micron $C^{18}$ silica HPLC column (4.6×150 mm) with a 20 μl injection volume and with a Hewlett-Packard 1100 Series Diode Array Detector® with the detector set to record at a wavelength of 270 nm. The HPLC column is used at ambient temperature. Room or ambient temperature refers to 20–25° C. All non-aqueous reactions were run under a nitrogen atmosphere for convenience and to maximize yields. Concentration at reduced pressure means that a rotary evaporator was used.

EXAMPLE 1

Batch Resin Treatment of Alatrofloxacin Mesylate

Alatrofloxacin mesylate (50 g), containing approximately 700 ppm of oligomer impurity in addition to other less polar impurities, was dissolved in 0.05% aqueous methanesulfonic acid (714 mL), and then Mitsubishl's Diacon HP-20® hydrophobic resin (50 g) was added. After stirring the resin slurry for 24 hours in the dark, the slurry was filtered and the solution was analyzed by High Pressure Liquid Chromatography (HPLC). (HPLC conditions were as described above). The filtered solution contained 19 ppm of oligomer impurity with an 80% recovered yield of alatrofloxacin mesylate. Oligomer had the following NMR ($^1$NMR DMSO $d_6$) δ: 9.98 (d, 1H); 8.79 (s, 1H); 8.51 (s, 1H), 8.45 (d, 1H), 8.16 (d 1H), 8.03 (d 1H), 7.92 (d 1H), 7.76(m 2H), 7.61(m 2H), 7.33(m 2H), 4.18(q 1H), 3.77(q 1H), 3.60(m 8H), 2.54(s 1H), 2.34(s 1H), 2.27(s 3H), 1.92(b.s. 2H), 1.72(b.s. 2H), 1.28(d 3H), 1.17(d 3H).

EXAMPLE 2

Resin Column Treatment of Alatrofloxacin Mesylate

Alatrofloxacin mesylate was dissolved in 10 to 40 liters of water per kilogram of drug substance at ambient temperature. The solution was filtered and then passed through (3–5 bed volumes per hour) a column containing hydrated Amberchrom CG-161® polystyrene resin (approximately 10–12 kg of crude reaction product per kilogram of dry resin). This column was washed with water (3 L/kg of crude reaction product), and then the eluant and wash were combined. The treated alatrofloxacin mesylate solution was analyzed by HPLC. Column treatment with the polystyrene resin reduced the impurity of formula II levels from 500 ppm to less than 30 ppm based on the drug substance. In addition, the drug was recovered in 95% yield from the resin.

EXAMPLE 3

Isolation of Zwitterion

A solution containing resin-treated alatrofloxacin mesylate (10 g)(prepared by Examples 1 or 2), deionized water (154 mL) and ethanol (31 mL) was neutralized to pH of about 6.5–7.5 by dropwise addition of 10% aqueous caustic. The suspension was granulated for 30 minutes at 24° C. and then filtered. After the filtered solids were rinsed with ethanol (30 mL), the zwitterion was dried in vacuo at 40° C. for approximately 16 hours. Alatrofloxacin (800 g) was recovered in 95% yield as white trapezoidal crystals.

EXAMPLE 4

Formation of Alatrofloxacin Mesylate

Alatrofloxacin zwitterion (25 g wet cake) as either a wet cake or dry product was combined with 10% aqueous ethanol (242 mL), and then methanesulfonic acid (1.9 mL) was added to the slurry to adjust the pH to about 3.5–4.5. The reaction mixture was then heated to reflux, filtered and then concentrated at atmospheric pressure to approximately one-half of its original volume. The solution was then cooled to 0–5° C., and the resulting solids were granulated for 1 hour. After the solids were filtered and washed with ethanol (39 mL), the alatrofloxacin mesylate was dried for 24 hours at 40° C. Alatrofloxacin mesylate (17.7 g), suitable for parenteral formulation, was isolated in 90% yield.

EXAMPLE 5

Parenteral Composition in Vials

Alatrofloxacin mesylate (314.46 mg prepared according to Example 4) was dissolved in a minimum amount of Water For Injection, United States Pharmacopeia (WFI). The pH of the resulting solution was adjusted to pH 4 with a 1% weight/weight (w/w) solution of hydrochloric acid, National Formulary (NF) in Water For Injection, and/or a 1% weight/weight (w/w) solution of sodium hydroxide, National Formulary, in Water For Injection and diluted to a concentration of 7.86 mg/mL. The resulting solution (40.12 grams) was filtered and filled into a 40 ml vial and stoppered. The stoppered vial was sterilized by autoclave at 115° C. for 15 minutes.

EXAMPLE 6

Parenteral Composition In Ampoules

Alatrofloxacin mesylate (314.4 mg prepared according to Example 4) was dissolved in a minimum amount of Water For Injection, United States Pharmacopeia (WFI). The pH of the resulting solution was adjusted to pH 4 with a 1% weight/weight (w/w) solution of hydrochloric acid, National Formulary (NF), in Water For Injection, and/or a 1% weight/weight (w/w) solution of sodium hydroxide, National Formulary, in Water For Injection and diluted to a concentration of 7.86 mg/ml. The resulting solution (40.12 grams) was filtered and filled into a 40 ml ampoule and sealed. The sealed ampoule was sterilized by autoclave at 115° C. for 15 minutes.

EXAMPLE 7

Lyophile

Alatrofloxacin mesylate (314.46 mg prepared according to Example 4) and lactose (500 mg, National Formulary) were dissolved in a sufficient amount of Water For Injection, United States Pharmacopeia, to yield a final weight of 10000 mg. The resulting solution was filtered and filed into a 20 ml vial. The filled vial was lyophilized for 24 hours under a vacuum of 0.1 atmospheres at which time the vial was stoppered and sealed. The sealed vial was sterilized by treatment in an autoclave at 115° C. for 15 minutes.

EXAMPLE 8

Isotonic Parenteral Composition In Vials

Dextrose (500 mg, United States Pharmacopeia) and alatrofloxacin mesylate (314.46 mg prepared according to Example 4) were dissolved in a minimum amount of Water For Injection (United States Pharmacopeia) and the pH was adjusted to pH 4 with a 1% w/w solution of hydrochloric acid (National Formulary) in Water For Injection and/or a 1% w/w solution of sodium hydroxide in Water For Injection (United States Pharmacopeia) and diluted to a concentration of 3.14 mg/ml. The resulting solution (101.7 grams) was filtered and filled into a 100 ml vial and stoppered. The stoppered vial was sterilized by autoclave at 115° C. for 15 minutes.

EXAMPLE 9

Isotonic Parenteral Composition Ampoules

Dextrose (500 mg, United States Pharmacopoeia) and alatrofloxacin mesylate (314.4 mg prepared according to Example 4) were dissolved in a minimum amount of Water For Injection (United States Pharmacopeia) and the pH was adjusted to pH 4 with a 1% w/w solution of hydrochloric acid (National Formulary) in Water For Injection and/or a 1% w/w solution of sodium hydroxide in Water For Injection (United States Pharmacopeia) and diluted to a concentration of 3.14 mg/mL. The resulting solution (101.7 grams) was filtered and filled into a 100 ml ampoule and sealed. The sealed ampoule was sterilized by autoclave at 115° C. for 15 minutes.

EXAMPLE 10

L-ALANYL-N-[3-[6-[[[3-[6-CARBOXY-8-(2,4-DIFLUOROPHENYL)-3-FLUORO-5,8-DIHYDRO-5-OXO-1,8-NAPHTHYRIDIN-2-YL]-3-AZABICYCLO[3.1.0]HEX-6-YL]AMINO]CARBONYL]-8-(2,4-DIFLUOROPHENYL)-3-FLUORO-5,8-DIHYDRO-5-OXO-1,8-NAPHTHYRIDIN-2-YL]-3-AZABICYCLO-[3.1.0]HEX-6-YL]-L-ALANINAMIDE, METHANESULFONATE

A 250 mL single-neck, round bottom flask was equipped with a reflux condenser and a magnetic stirring bar. The flask was purged and then maintained under a dry nitrogen atmosphere. (1α, 5α, 6α)-7-(6-Amino-3-azabicyclo[3.1.0]hex-3-yl)-1-(2,4-difluorophenyl)-6-fluoro-1,4-dihydro-4-oxo-1,8-naphthyridine-3-carboxylic acid, ethyl ester (2.50 g, 5.62 mmol) (prepared according to the method described in International Patent Publication WO 97/00268); (1α, 5α, 6α)-N-[(1,1-dimethylethoxy)carbonyl]-L-alanyl-N-[3-[-(2,4-difluorophenyl)-6-carboxy-3-fluoro-5,8-dihydro-5-oxo-1,8-naphthyridin-2-yl]-3-azabicyclo[3.1.0]hex-6-yl]-L-alaninamide (3.37 g, 5.11 mmol) (prepared according to the method described in International Patent Publication WO 97/08191), and 100 mL of methylene chloride were added to the flask affording a white slurry. After 4-dimethylaminopyridine (0.37 g, 3.07 mmol) and bromo-tris-pyrrolidino-phosphonium hexafluorophosphate (2.86 g, 6.14 mmol) were added to the reaction mixture, 1.8 mL of diisopropylethylamine (10.2 mmol) was slowly added over 30 minutes. The reaction mixture was stirred at 25–30° C. overnight, and then thin-layer chromatography [Merck Kieselgel 60 $F_{254}$ silica plates (5×10 cm) using an ammonium hydroxide/methanol/methylene chloride (1:10:90) eluant] showed that the reaction was complete. The thick slurry was filtered, the filter cake washed with methylene chloride (2×20 mL), and then dried in vacuo at 25–30° C. to give 4.63 9 (83% yield) of a diprotected intermediate, a precursor to compound of Formula II. $^1$H NMR (CDCl3): δ8.58 (s, 1 H), 8.35 (s, 1H), 8.02 (d, J=12.7 Hz, 1H), 7.96 (d, J=12.5 Hz, 1H), 7.33 (m, 2), 7.05 ( m, 6H), 6.70 (m, 1H), 5.24 (m, 1H), 4.39 (q, J=7.26 Hz, 1H), 4.3:3 (q, J=726 Hz, 2H), 4.03 (q, J=1.7 Hz, 1H), 3.87 (m, 4H), 3.55 (m, 4H ), 2.66 (s, 1H), 2.40 (s, 1H), 1.87 (m, 4H), 1.41 (s, 9H), and 1.35 (m, 9H); FABMS: m/z 1086 (MH$^+$).

Methanesulfonic acid (1.4 mL) and water (3.1 mL) were added to the diprotected intermediate (4.63 g, 4.28 mmol) suspended in 135 mL of 1-methyl-2-pyrrolidinone. A solution was formed after heating the reaction mixture for 15 minutes 80–85° C. and the reaction was essentially complete after heating for an additional 48–58 hours at 80–85° C. The solution was cooled to room temperature and 270 mL of methylene chloride was slowly added. The resulting slurry was stirred for 2 days at room temperature and then filtered. The solid was dried at reduced pressure to afford 4.0 g of crude product. The granular solid was ground in a mortar and pestle and then slurried and with 160 ml of methylene chloride. After stirring the slurry for 24 hours at room temperature, the solid was filtered and then air dried to give the compound of formula II as the mesylate salt (3.20 g, 75% yield). $^1$H NMR (DMSO-d$_6$): δ9.98 (d, 1 H), 8.79 (s, 1H), 8.51 (s, 1H), 8.45 (d, 1H), 8.16 (d, 1H), 8.03 (d, J=12.6 Hz, 1H), 7.92 (d, J=12.9 Hz,1H), 7.76 (m, 2H), 7.61 (m, 2H), 7.33 (m, 2H), 4.18 (q, J=6.85 Hz, 1H), 3.77 (q, J=7.06 Hz, 1H), 3.60 (m, 8H), 2.54 (s, 1H), 2.34 (s, 1H), 2.27 (s, 3H), 1.92 (s, 2H), 1.72 (s, 2H), 1.28 (d, J=6.85 Hz, 3H), and 1.17 (d, J=7.06 Hz, 3H); FABMS: m/z 957 M$^{-CH3SO3H}$).

EXAMPLE 11

(1α, 5α, 6α)-7-(6-[7-(6-AMINO-3-AZABICYCLO[3.1.0]HEX-3-YL)-1-(2,4-DIFLUOROPHENYL)-6-FLUORO4-OXO-1,4-DIHYDRO-1,8-NAPHTHYRIDINE-3-CARBOXAMIDO]-(1α, 5α, 6α)-3-AZABICYCLO[3.1.0]HEX-3-YL)-1-(2,4-DIFLUOROPHENYL)-6-FLUORO-4-OXO-1,4-DIHYDRO-1,8-NAPHTHYRIDINE-3-CARBOXYLIC ACID, METHANESULFONATE

To a 20 mL round bottom flask which was equipped with a reflux condenser, a magnetic stirring bar, and a nitrogen inlet was added (1α, 5α, 6α)-1-(2,4-difluorophenyl)-7-[6-[[(1,1-dimethylethoxy)carbonyl]amino]-3-azabicyclo[3.1.0]hex-3-yl)-6-fluoro-1,4-dihydro4-oxo-1,8-naphthyridine-3-carboxylic acid (232 mg, 0.45 mmol) (prepared according to the method described in U.S. Pat. No. 5,164,402), triethylamine (1.14 g, 11.3 mmol), 2.0 mL of a 50%(w/w) solution of 1-propanephosphonic acid cyclic anhydride (1.43 g, 4.50 mmol) in ethyl acetate, and 10 mL of tetrahydrofuran (THF). The resulting slightly yellow suspension was maintained under an inert nitrogen atmosphere. In a separate flask which was equipped with a magnetic stirring bar and pressure-qualizing addition funnel, a suspension of (1α, 5α, 6α)-7-(6-amino-3-azabicyclo[3.1.0]hex-3-yl)-1-(2,4-difluorophenyl)-6-fluoro-1,4-dihydro-4-oxo-1,8-naphthyridine-3-carboxylic acid, ethyl ester (200 mg, 0.45 mmol) (prepared according to the method described in International Patent Publication WO 97/00268); in 5 mL of THF was prepared. The yellow suspension containing the triethylamine was poured into the addition funnel and then slowly added over 20 minutes to the flask containing (1α, 5α, 6α)-7-(6-amino-3-azabicyclo[3.1.0]hex-3-yl)-1-(2,4-difluorophenyl)-6-fluoro-1,4-dihydro-4-oxo-1,8-naphthyridine-3-carboxyiic acid, ethyl ester. The mixture was stirred for 6 hours at room temperature when thin-layer chromatography lMerck Kieselgel 60 $F_{254}$ silica plates (5×10 cm) using a methanol/methylene chloride (1:9) eluant] showed that the reaction was complete. The yellow suspension was poured into 70 mL of water and the pH was adjusted to 3.0 with 2 N hydrochloric acid. The aqueous solution was extracted with 70 mL of methylene chloride and then the methylene chloride solution was washed with water (70 mL). The methylene chloride was removed at reduced pressure to afford a crude solid (449 mg) which was triturated with 6 mL of ethanol for 6 hours. The slurry was filtered, the solid washed with 2 mL of ethanol and then dried in vacuo for 18 hours at 45° C. to afford 304 mg (72% yield) of the diprotected intermediate to the compound of Formula III as a white crystalline solid. Mp 248–251° C.; $^1$H NMR (CDCl3): δ10.0 (d, 2H), 8.60 (s, 1 H), 8.35 (s, 1H), 8.05 (d, 1H), 7.96 (d, 1H), 7.33 (m, 2), 7.05 ( m, 4H), 4.70 (m, 1H), 4.36 (q, 2H), 3.92 (m, 3H), 3.05 (m, 3H ), 2.68 (s, 1H), 2.23 (s, 1H), 1.86 (m, 2H), 1.77 (m, 2H) 1.59 (s, 9H), and 1.38 (t, 3H); FABMS: m/z 943 (M$^+$).

Methanesulfonic acid (0.07 mL) and water (0.16 mL) were added to the diprotected intermediate (240 mg, 0.25 mmol) suspended in 7 mL of 1-methyl-2-pyrrolidinone. The reaction mixture was heated for 50–58 hours at 80–85° C. The solution was then cooled to room temperature and 14 mL of methylene chloride was slowly added. The resulting slurry was stirred for 2 days at room temperature and then filtered. The solid was dried at reduced pressure to afford 110 mg of crude product. The crude solid was triturated with 3 mL of methylene chloridelmethanol (1:1) for 4 hours and then filtered. The solid was dried in vacuo at 45° C. to give the compound of formula IIII as its mesylate salt (105 mg, 45% yield). Melting Point: Greater than 230° C.; $^1$H NMR recorded in trifluoroacetic acid showed the absence of the BOC and ethyl ester protecting groups and it was consistent with the structure of the compound of Formula Ill;

FABMS: m/z 815 (M$^{-CH3SO3H}$).

What is claimed is:

1. A process of purifiing a compound of the formula

I comprising, treating an impure reaction product containing an amount of said compound of formula I and less polar impurities, with a hydrophobic resin.

2. A process according to claim 1, wherein said less polar impurities have a retention time of about 2.1 to about 30 minutes.

3. A process according to claim 1, wherein one of said less polar impurities has a retention time of about 9 to about 12 minutes.

4. A process according to claim 1, wherein one of said less polar impurities has the formula

5. A process according to claim 1, wherein said impurities, after treatment, comprise less than about 60 ppm relative to the total weight of the purified product.

6. A process according to claim 1, wherein said impurities, after treatment, comprise less than about 20 ppm relative to the total weight of the purified product.

7. A process according to claim 1, wherein said hydrophobic resin is a crosslinked polystyrene resin.

8. A compound of the formula substantially free of less polar impurities.

9. A compound according to claim 8, wherein said compound of formula I is substantially free of a compound of formula II 10. A parenteral composition, comprising an antibacterially effective amount of a compound of the formula I, or a pharmaceutically acceptable salt thereof, substantially free of less polar impurities, and a pharmaceutically acceptable carrier.

11. A parenteral composition, comprising an antibacterially effective amount of a compound of the formula I, or a pharmaceutically acceptable salt thereof, substantially free of a compound of formula II and a pharmaceutically acceptable carrier.

12. A parenteral composition according to claim 8, comprising a compound of formula I and water.

13. A parenteral composition according to claim 8, wherein the compound of formula I is a lyophylate.

14. A parenteral composition according to claim 9, wherein the compound of formula I comprises about 10 mg to about 700 mg of compound in a unit dosage container.

15. A parenteral composition according to claim 9, wherein the compound of formula I comprises about 275 mg to about 500 mg of compound in a unit dosage container.

16. A parenteral composition according to claim 8, wherein the compound of formula I comprises about 10 mg to about 700 mg of compound in a unit dosage container.

17. A parenteral composition according to claim 8, wherein the compound of formula I comprises about 275 mg to about 500 mg of compound in a unit dosage container.

18. A compound of the formula

II

19. A pharmaceutical composition, comprising an antibacterially effective amount of a compound according to claim 18, or a pharmaceutically acceptable salt thereof.

20. A method of treating a bacterial infection, comprising administering to a subject affected by a bacterial infection an antibacterially effective amount of a compound according to claim 18.

21. A compound of formula IIII

III

22. A pharmaceutical composition, comprising an antibacterially effective amount of a compound according to claim 21, or a pharmaceutically acceptable salt thereof.

23. A method of treating a bacterial infection, comprising administering to a subject affected by a bacterial infection an antibacterially effective amount of a compound according to claim 21.

24. The composition of claim 8 wherein said impurities comprise less than about 60 ppm relative to the total weight of the composition.

25. The composition of claim 8 wherein said impurities comprise less than about 20 ppm relative to the total weight of the composition.

* * * * *